US010744092B2

(12) United States Patent
Yuk (10) Patent No.: US 10,744,092 B2
(45) Date of Patent: Aug. 18, 2020

(54) TEMPERATURE-SENSITIVE COMPOSITE AND METHOD FOR PREPARING SAME

(71) Applicant: KOREA UNIVERSITY RESEARCH AND BUSINESS FOUNDATION, SEJONG CAMPUS, Sejong-si (KR)

(72) Inventor: Soon Hong Yuk, Gyeonggi-do (KR)

(73) Assignee: Korea University Research and Business Foundation, Sejong Campus, Sejong-si (KR)

( * ) Notice: Subject to any disclaimer, the term of this patent is extended or adjusted under 35 U.S.C. 154(b) by 0 days.

(21) Appl. No.: 16/079,142

(22) PCT Filed: Mar. 14, 2017

(86) PCT No.: PCT/KR2017/002709
§ 371 (c)(1),
(2) Date: Aug. 23, 2018

(87) PCT Pub. No.: WO2017/164555
PCT Pub. Date: Sep. 28, 2017

(65) Prior Publication Data
US 2019/0046447 A1 Feb. 14, 2019

(30) Foreign Application Priority Data

Mar. 22, 2016 (KR) .................. 10-2016-0033960

(51) Int. Cl.
*A61K 9/14* (2006.01)
*B82Y 5/00* (2011.01)
(Continued)

(52) U.S. Cl.
CPC ............ *A61K 9/146* (2013.01); *A61K 31/192* (2013.01); *A61K 31/337* (2013.01);
(Continued)

(58) Field of Classification Search
None
See application file for complete search history.

(56) References Cited

U.S. PATENT DOCUMENTS 5,206,262 A * 4/1993 Donati ................ A61K 31/205
514/428
8,992,949 B1 3/2015 Yang
(Continued)

FOREIGN PATENT DOCUMENTS

KR 10-2007-0100701 A 10/2007
KR 10-2012-0001194 A 1/2012
(Continued)

OTHER PUBLICATIONS

H Wang, P Agrawal, S Zhao, RX Xu, J Yu, X Lu, X He. "Hyaluronic acid-decorated dual responsive nanoparticles of Pluronic F127, PLGA, and chitosan for targeted co-delivery of doxorubicin and irinotecan to eliminate cancer stem-like cells." Biomaterials, vol. 72, pp. 74-89, available Aug. 29, 2015. (Year: 2015).*
(Continued)

*Primary Examiner* — Isaac Shomer
(74) *Attorney, Agent, or Firm* — Hammer & Associates, P.C.

(57) ABSTRACT

The present invention relates to a temperature-sensitive composite and a method for preparing the same. The temperature-sensitive composite according to the present invention is maintained in a liquid state at room temperature and solidified at the time of delivery in the body, and shows remarkably excellent improvement in mechanical properties compared with an existing temperature-sensitive polymer composite, and as a result, the temperature-sensitive composite can promote the stability of a drug delivery system in the body and the sustainment of drug release.

2 Claims, 12 Drawing Sheets

SCHEMATIC DIAGRAM OF TEMPERATURE-SENSITIVE NANOPARTICLE COMPOSITE ACCORDING TO EXAMPLE 3 OF THE PRESENT INVENTION (51) Int. Cl.
A61K 31/65 (2006.01)
A61K 31/445 (2006.01)
A61K 31/704 (2006.01)
A61K 31/192 (2006.01)
A61K 31/337 (2006.01)

(52) U.S. Cl.
CPC ............ A61K 31/445 (2013.01); A61K 31/65 (2013.01); A61K 31/704 (2013.01); B82Y 5/00 (2013.01); Y10S 977/773 (2013.01); Y10S 977/906 (2013.01)

(56) References Cited

U.S. PATENT DOCUMENTS

| | | | |
|---|---|---|---|
| 2012/0225017 A1* | 9/2012 | Gombotz | A61K 31/704 424/9.1 |
| 2012/0294806 A1* | 11/2012 | Chen | A61K 9/5115 424/9.3 |
| 2015/0010616 A1* | 1/2015 | Yuk | A61K 9/1271 424/450 |
| 2015/0366975 A1* | 12/2015 | Jhan | A61K 9/0024 514/34 |

FOREIGN PATENT DOCUMENTS

| | | |
|---|---|---|
| KR | 10-2012-0106412 | 9/2012 |
| KR | 10-2013-0084916 | 7/2013 |
| WO | 2006047279 A2 | 5/2006 |
| WO | 2007114552 A1 | 10/2007 |

OTHER PUBLICATIONS

SD Singh-Joy, VC McLain. "Safety Assessment of Poloxamers 101, 105, 108, 122, 123, 124, 181, 182, 183, 184, 185, 188, 212, 215, 217, 231, 234, . . . and Poloxamer 182 Dibenzoate as Used in Cosmetics." International Journal of Toxicology, vol. 27 (Suppl. 2), pp. 93-128. (Year: 2008).*

KH Bae, SH Choi, SY Park, Y Lee, TG Park. "Thermosensitive Pluronic Micelles Stabilized by Shell Cross-Linking with Gold Nanoparticles." Langmuir, vol. 22, 2006, pp. 6380-6384. (Year: 2006).*

SH Choi, SH Lee, TG Park. "Temperature-Sensitive Pluronic/Poly(ethylenimine) Nanocapsules for Thermally Triggered Disruption of Intracellular Endosomal Compartment." Biomacromolecules, vol. 7, 2006, pp. 1864-1870. (Year: 2006).*

SM Berge, LD Bighley, DC Monkhouse. "Pharmaceutical Salts." Journal of Pharmaceutical Sciences, vol. 66 No. 1, Jan. 1977, pp. 1-19. (Year: 1977).*

Y Lee et al. "Thermo-sensitive, injectable, and tissue adhesive sol-gel transition hyaluronic acid/pluronic composite hydrogels prepared from bio-inspired catechol-thiol reaction." Soft Matter, vol. 6, 2010, pp. 977-983. (Year: 2010).*

R Basak, R Bandyopadhyay. "Encapsulation of Hydrophobic Drugs in Pluronic F127 Micelles: Effects of Drug Hydrophobicity, Solution Temperature, and pH." Langmuir, vol. 29, 2013, pp. 4350-4356. (Year: 2013).*

N Roy, N Saha, T Kitano, P Saha. "Novel Hydrogels of PVP-CMC and Their Swelling Effect on Viscoelastic Properties." Journal of Applied Polymer Science, vol. 117, 2010, pp. 1703-1710. (Year: 2010).*

DM Faulkner et al. "A New Stable Pluronic® F68 Gel Carrier for Antibiotics in Contaminated Wound Treatment." American Journal of Emergency Medicine, vol. 15, 1997, pp. 20-24. (Year: 1997).*

JV Cauich-Rodriguez, S Deb, R Smith. "Physicochemical Characterization of Hydrogels Based on Polyvinyl Alcohol-Vinyl Acetate Blends." Journal of Applied Polymer Science, vol. 82, 2001, pp. 3578-3590. (Year: 2001).*

Hai Wang et al., "Hyaluronic acid-decorated dual responsive nanoparticles of Pluronic F127, PLGA, and chitosan for targeted co-delivery of doxorubicin and irinotecan to eliminate cancer stem-like cells," Biomaterials, Elsevier Ltd., (vol. 72), (p. 74-89), (2015).

Shu Chen et al., "Temperature-Responsive Magnetite/PEO-PPO-PEO Block Copolymer Nanoparticles for Controlled Drug Targeting Delivery," Langmuir, American Chemical Society, (vol. 23), (p. 12669-12676), (2007).

Shu-Hui Hsu et al., "Physicochemical Characterization and Drug Release of Thermosensitive Hydrogels Composed of a Hyaluronic Acid/Pluronic F127 Graft," Chem. Pharm. Bull., Pharmaceutical Society of Japan, (vol. 57), (Issue. 5), (p. 453-458), (2009).

Keun Sang Oh et al., "Sol-gel transition of nanoparticles/polymer mixtures for sustained delivery of exenatide to treat type 2 diabetes mellitus," European Journal of Pharmaceutics and Biopharmaceutics, Elsevier B.V., (vol. 88), (p. 664-669), (2014).

* cited by examiner

SCHEMATIC DIAGRAM OF TEMPERATURE-SENSITIVE POLYMER/NANOPARTICLE COMPOSITE ACCORDING TO EXAMPLES 1 AND 2 OF THE PRESENT INVENTION

[Figure 3]

SCHEMATIC DIAGRAM OF TEMPERATURE-SENSITIVE
NANOPARTICLE COMPOSITE ACCORDING TO EXAMPLE 3
OF THE PRESENT INVENTION

TEMPERATURE-SENSITIVE COMPOSITE AND METHOD FOR PREPARING SAME

TECHNICAL FIELD

The present invention relates to a temperature-sensitive composite and a method for preparing the same.

BACKGROUND ART

With understanding the action principle of a temperature-sensitive hydrogel, numerous application and development have been reported. For example, a polymer mixture composed of Pluronic F-127 exhibiting a temperature-induced phase transition and sodium hyaluronate controlling viscosity maintained its liquid state at room temperature and solidified at the time of delivery into the body through injection. Thereby being stabilized in a wound has been suggested [Korean Unexamined Patent Application Publication No. 2007-0100701; Patent Document 1] and an investigation example using a copolymer of Pluronic F-127 and sodium hyaluronate as a delivery system for an anti-cancer agent has been suggested [Chem Pharm Bull 57(5) 453-458 (2009); Non-Patent Document 1]. Recently, the inventors reported a nanoparticle/hydrogel composite (exenatide-loaded Pluronic F-68 nanoparticles with F-127) and a blood sugar regulatory effect was demonstrated for three days or longer with one administration [European Journal of Pharmaceutics and Biopharmaceutics 88, 664-669 (2014); Non-Patent Document 2].

However, because the above-mentioned drug delivery systems are dependent on the concentration of the polymer of the delivery system, they are easily solubilized (or disintegrated) when administered so that a fast drug release state due to instability is exhibited. Particularly, when a water-soluble drug or protein drug and antibodies are contained, due to excellent solubility in an aqueous solution, fast drug release is induced, and thus it is difficult to realize the desired efficacy. To overcome these difficulties, repeated administration of a drug is required and an increase in treatment cost is expected in the case of an expensive protein drug or antibody. As alternatives as presented in Patent Document 1, a combination of a temperature-sensitive polymer and various types of drug-loaded nanoparticles was used, but remarkable improvement in efficacy was not achieved with the composite material of a polymer and nanoparticles.

Accordingly, there is a demand for a novel type of temperature-sensitive composite which has increased stability in the body, maintains excellent redispersibility in an aqueous solution when prepared in the form of powder, and exhibits sustained drug efficacy by controlling a drug release rate.

DISCLOSURE

Technical Problem

Therefore, the inventors had attempted to solve such problems, thereby developing a novel temperature-sensitive drug delivery vehicle with sustained release pattern, which includes: nanoparticles including a biocompatible polymer exhibiting a temperature-induced phase transition and a drug; and a diluent, and thus the present invention was completed.

Technical Solution

As a means for achieving the above-mentioned object, the present invention provides a temperature-sensitive composite, which includes: nanoparticles including a biocompatible polymer exhibiting a temperature-induced phase transition and a drug; and a diluent.

Advantageous Effects

A temperature-sensitive composite of the present invention can be used as a drug delivery system, which maintains stability, shows excellent redispersibility in an aqueous solution when prepared in the form of powder, and exhibits sustained drug release by controlling a drug release rate.

Particularly, nanoparticles, which are a component of the temperature-sensitive composite according to the present invention, consist of a Pluronic polymer having a hydrophilic surface, and thus can be very useful for delivery of hydrophobic drug with low solubility.

BEST MODE

The term "temperature-induced phase transition" used herein refers to the Sol-Gel phase transition in which a temperature-induced phase transition polymer (e.g., Pluronic) solution is maintained in a liquid (sol) phase at a specific temperature or less, and solidified (gel) when the environment is maintained at a specific temperature or more. This is because the critical micelle concentration (CMC) of Pluronic depending on temperature (see Non-Patent Document 2).

A biocompatible polymer exhibiting the temperature-induced phase transition contains a drug, which is associated with a particle surface by surrounding the drug, and may be, specifically, a poly(ethylene oxide)-poly(propylene oxide)-poly(ethylene oxide) (PEO-PPO-PEO) copolymer.

The PEO-PPO-PEO copolymer is a triblock copolymer represented by Formula 1.

Formula 1

In Formula 1, b is an integer of 10 or more, and a+c is a number allowing the ends of the formula, for example, $((C_2H_4O)_a$ and $(C_2H_4O)_c)$, to be included at 5 to 95 wt %, and preferably 20 to 90 wt % of the PEO-PPO-PEO copolymer.

Properties of the PEO-PPO-PEO copolymer depend on a ratio of a polyoxypropylene block and a polyoxyethylene block, that is, a ratio of b and a+c in Formula 1. The PEO-PPO-PEO copolymer may be a commercially available product which is prepared by a method described in the known literature or previously prepared. The PEO-PPO-PEO copolymer used in the method for preparing the present invention is not particularly limited, but may have a molecular weight of approximately 1,000 to 16,000.

Meanwhile, the PEO-PPO-PEO copolymer is known as a poloxamer or Pluronic. A poloxamer is a solid at room temperature and is soluble in water and ethanol. According to an exemplary embodiment of the present invention, the PEO-PPO-PEO copolymer may be at least one selected from the group consisting of Pluronic F-68, Pluronic F-127, Pluronic F-188, Pluronic F-237, Pluronic F-338 and Pluronic F-407, but the present invention is not limited thereto. For example, Pluronic F-188 is a compound in which b is 30 and a+c is 75 in Formula 1, and refers to a poloxamer having a molecular weight of approximately 8,350. In addition, when Pluronic F-127 is contained at 20 wt %, a gel (solidified) is formed at room temperature (25° C.). When the concentration of Pluronic F-127 is diluted to 15 wt %, Pluronic F-127 has a property of forming a gel at approximately 30° C.

The drug includes a poorly-soluble drug, water-soluble drug, a protein drug, and, a contrast agent for molecular imaging, but the present invention is not limited thereto. The poorly-soluble drug refers to a drug with low solubility in the aqueous media, and also refers to a hydrophobic drug, for example, an anti-cancer agent, or a drug for a cardiovascular disease such as arteriosclerosis, hyperlipidemia or the like, but the present invention is not limited thereto. Specifically, the poorly-soluble drug includes, for example, paclitaxel, docetaxel, tamoxin, anastrozole, carboplatin, topotecan, belotecan, imatinib, irinotecan, floxuridine, vinorelbine, gemcitabine, leuprolide, flutamide, zoledronate, methotrexate, camptothecin, cisplatin, vincristine, hydroxyurea, streptozocin, valrubicin, lovastatin, simvastatin, fluvastatin, atorvastatin, pitavastatin, pravastatin, rosuvastatin or the like, but the present invention is not limited thereto. The water-soluble drug refers to a drug with high solubility in the aqueous media, for example, bupivacaine, ropivacaine, doxorubicin or the like, but the present invention is not limited thereto. Most of the protein drugs have a surface charge, which may be a positive or negative charge under physiological conditions according to the isoelectric point of the protein, and may also be referred to as an ionic drug. The protein drug includes exenatide, erythropoietin, vascular endothelial growth factor (VEGF), TGF-beta or the like, but the present invention is not limited thereto.

The nanoparticles containing a biocompatible polymer exhibiting the temperature-induced phase transition and a drug are nanoparticles in which a drug is surrounded by or loaded in a biocompatible polymer exhibiting a temperature-induced transition as a shell. Specifically, the nanoparticles of the present invention may be biocompatible nanoparticles in which the drug-containing nanoparticles prepared by the present inventor are encapsulated, and a PEO-PPO-PEO copolymer is associated with the surface thereof [A specific description is the same as described in Korean Unexamined Patent Application Publication No. 2013-0084916], or nanoparticles in which a nano lipid nucleus is present in a shell consisting of a PEO-PPO-PEO copolymer matrix and a drug are adsorbed onto the surface of the nano lipid nucleus [A specific description is the same as described in Korean Unexamined Patent Application Publication No. 2007-0099767], but the present invention is not limited thereto.

The diluent allows the polymer to be diluted to a suitable concentration by controlling viscosity such that the polymer is maintained in a liquid phase at room temperature and a solid phase such as a gel is maintained at a body temperature, and may be, for example, sodium hyaluronate; or biocompatible and water-soluble nanoparticles including a polymer capable of controlling viscosity and a drug. The nanoparticles used as a diluent may be nanoparticles in which a nano lipid nucleus is present in a shell formed of a PEO-PPO-PEO copolymer matrix previously prepared by the inventor according to Korean Unexamined Patent Application Publication No. 2007-0099767, and a drug is adsorbed onto the surface of the nano lipid nucleus. Particularly, the biocompatible and water-soluble polymer capable of controlling viscosity may be one or more selected from the group consisting of Pluronic F-68, polyvinyl alcohol (PVA), poly]vinylpyrrolidone and polyvinyl acetate, but the present invention is not limited thereto. For example, Pluronic F-68 has a property in which a 35 wt % aqueous solution thereof forms a gel at 50° C. or more.

The temperature-sensitive composite according to the present invention is maintained in a liquid phase at room temperature, maintained in a solid phase such as a gel at a body temperature, exhibits stability and redispersibility, and shows sustained release of a drug, and therefore can be used as a drug delivery system.

Accordingly, the present invention includes a drug delivery system including the temperature-sensitive composite.

In addition, the present invention provides a method for preparing a temperature-sensitive composite, which includes:

preparing nanoparticles which include a biocompatible polymer exhibiting a temperature-induced phase transition and a drug; and mixing the nanoparticles with a diluent.

All of the above-described contents relating to the temperature-sensitive composite can be directly applied or applied to the method for preparing a temperature-sensitive composite.

First, in the step of preparing nanoparticles including a biocompatible polymer exhibiting a temperature-induced phase transition and a drug, nanoparticles in which a drug is surrounded by or loaded in a biocompatible polymer showing a temperature-induced phase transition as a shell are prepared.

Specifically, biocompatible nanoparticles in which drug-containing nanoparticles previously prepared by the inventor using a temperature-induced phase transition method according to Korean Unexamined Patent Application Publication No. 2013-0084916 are encapsulated and a PEO-PPO-PEO copolymer is associated with the surface thereof may be prepared, or nanoparticles in which a nano lipid nucleus is present in a shell consisting of a PEO-PPO-PEO copolymer matrix using the microencapsulation method according to Korean Unexamined Patent Application Publication No. 2007-0099767, and a drug is adsorbed onto the surface of the nano lipid nucleus may be prepared, but the present invention is not limited thereto.

A temperature-sensitive composite is prepared by mixing the nanoparticles prepared above with a diluent.

The temperature-sensitive composite in the present invention prepared by the above-described method may be easily redispersed while being dissolved by dispersing the composite in a solution such as an aqueous solution for administration to the body. In addition, since the temperature-sensitive composite may be prepared by a simple method using a biocompatible polymer without using an organic solvent or other excipients exhibiting adverse effect on a human body, both of stability and ease of process may be achieved. In addition, the temperature-sensitive composite has improved stability, and thus can be used as a pharmaceutical agent in various ways.

MODES OF THE INVENTION

Hereinafter, the present invention will be described in further detail with reference to examples according to the present invention, but the scope of the present invention is not limited to the following examples.

EXAMPLES

Example 1: Preparation of Temperature-Sensitive Composite Which Consists of Sodium Hyaluronate (SH) and Hydrophobic Drug (Naproxen)-Loaded Pluronic F-127 Nanoparticles Nanoparticles including Pluronic F-127 and a drug were prepared using a temperature-induced phase transition method described in Korean Unexamined Patent Application Publication No. 2013-0084916.

Briefly, a uniform composite was prepared by mixing 0.4 g of naproxen and 0.1 g of polyethylene glycol 400 (PEG 400) for 12 hours. 0.4 g of poloxamer (polyoxyethylene-polyoxypropylene-polyoxyethylene triblock copolymer, Pluronic F-127) was added to the mixture, and the subsequent mixture was heated at 70° C. for 10 minutes and stirred for 5 minutes. Then when the mixture was completely melted and had become a liquid viscous material, stirring was stopped, and the mixture was cooled at room temperature to obtain nanoparticles.

Separately, a sodium hyaluronate aqueous solution was prepared by mixing 50 mg of sodium hyaluronate with 10 ml of distilled water, and a composite aqueous solution was prepared by further adding 2 g of the nanoparticles prepared above to the aqueous solution, thereby preparing a composite aqueous solution.

If necessary, the composite aqueous solution prepared above was stored by lyophilization. For use, the lyophilized product was redispersed in an aqueous solution. As a result, a temperature-sensitive composite consisting of hydrophobic drug (naproxen)-loaded Pluronic F-127 nanoparticles was prepared.

Figure 1:
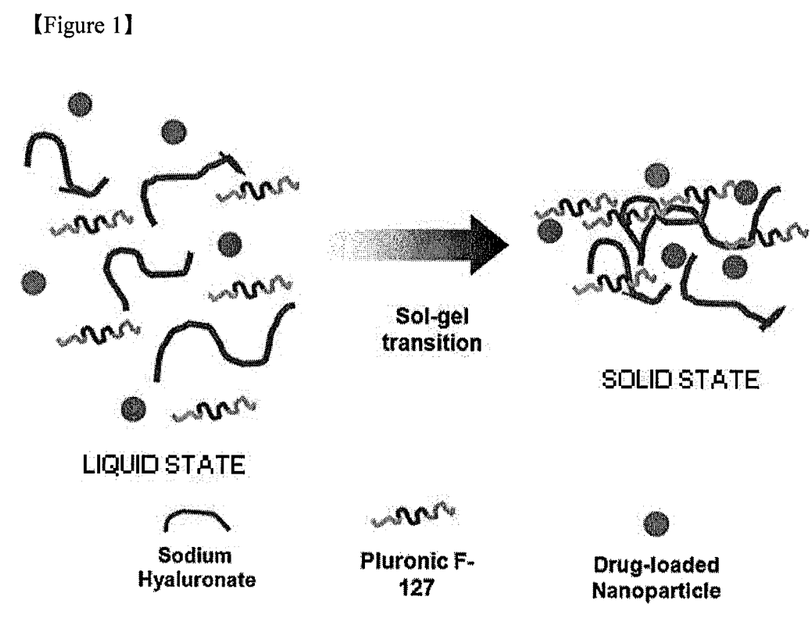
FIG. 1 is a schematic diagram of a temperature-sensitive composite according to Korean Unexamined Patent Application Publication No. 2007-0100701.
Figure 2:
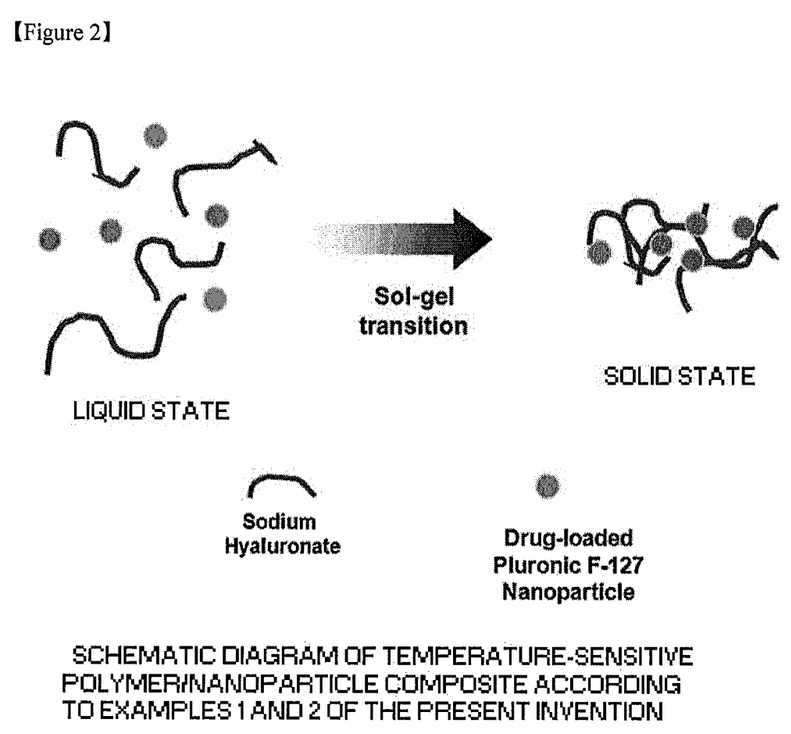
FIG. 2 is a schematic diagram of a temperature-sensitive nanoparticle/diluent composite according to Examples 1 and 2 of the present invention.
Figure 3:
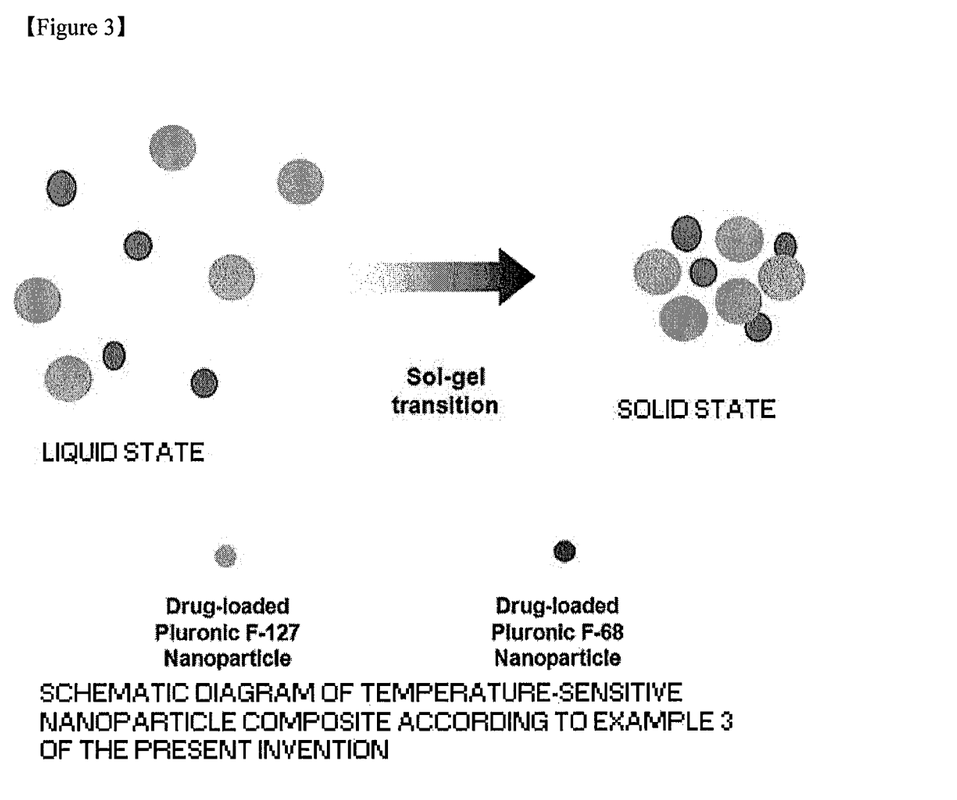
FIG. 3 is a schematic diagram of a temperature-sensitive nanoparticle/diluent composite according to Example 3 of the present invention.
Figure 4:
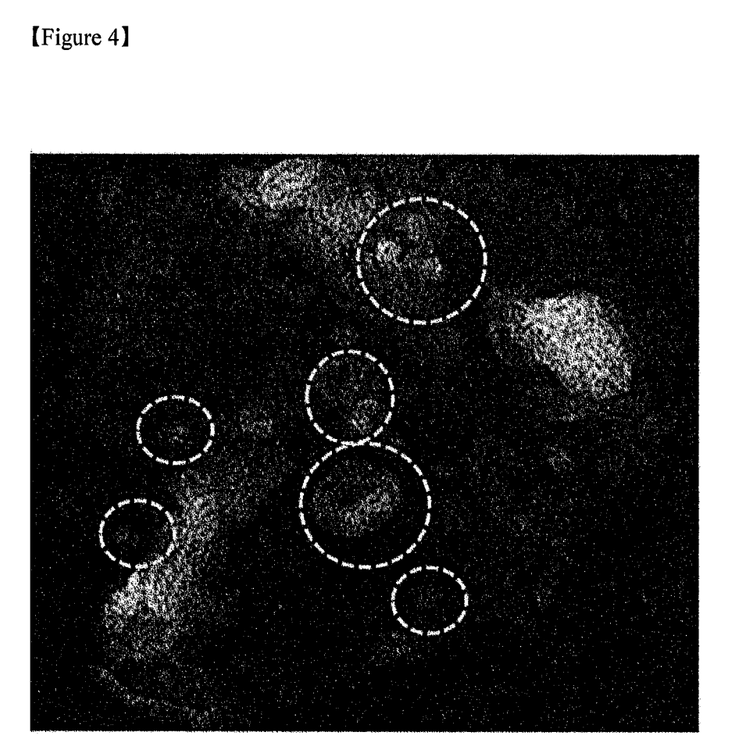
FIG. 4 is a transmission electron microscopy (TEM) image of a temperature-sensitive composite prepared according to Example 1 [nanoparticles containing naproxen (marked with dotted circles) are dispersed in an SH network].
Figure 5:
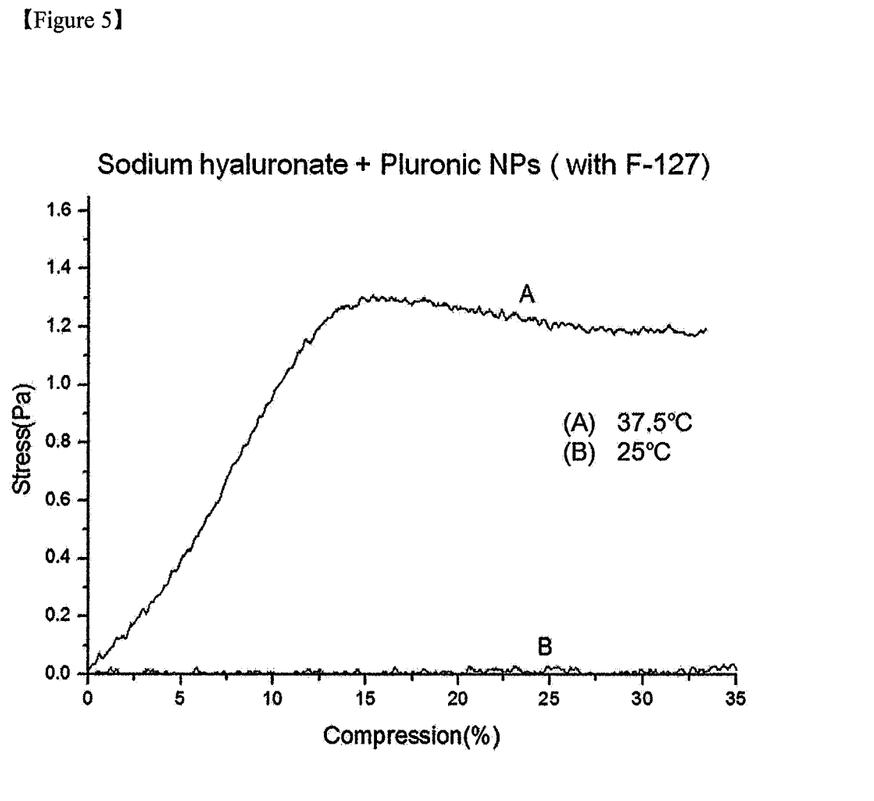
FIG. 5 is a graph showing a change in mechanical strength of a composite consisting of sodium hyaluronate and drug-loaded Pluronic F-127 nanoparticles in response to temperature change from room temperature (25° C.) to a body temperature (37.5° C.) (Examples 1 and 2).
Figure 7:
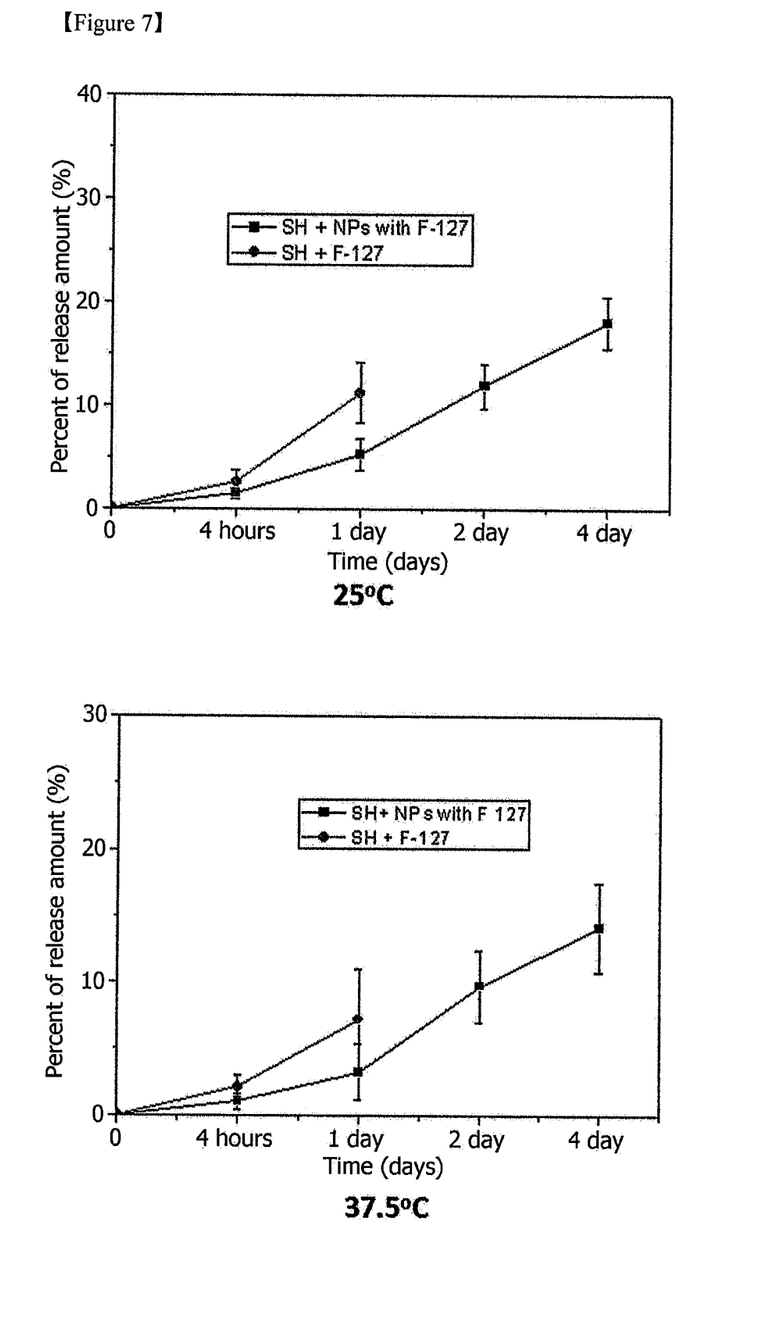
FIG. 7 is a set of graphs showing release patterns of a drug (naproxen) from composites according to Example 1 and Comparative Example 1 over time at room temperature and a body temperature [SH+NPs with F-127: Example 1, SH+F-127: Comparative Example 1].

The mechanical properties of the temperature-sensitive composite were measured (the result is the same as shown in FIG. 5 within an error range), and a change in drug release over time was measured (FIG. 7).

Example 2: Preparation of Temperature-Sensitive Composite Which Consists of Sodium Hyaluronate (SH) and Ionic Drug (Bupivacaine)-Loaded Pluronic F-127 Nanoparticles Nanoparticles including Pluronic F-127 and a drug were prepared using a temperature-induced phase transition method described in Korean Unexamined Patent Application Publication No. 2007-0099767.

Using ultrasonication, a 20 wt % lecithin aqueous solution was prepared. At this time, lecithin nanoparticles having a diameter of approximately 65 nm were formed. 0.1 g of bupivacaine was added to and mixed with the 1 ml of the lecithin nanoparticle aqueous solution. A 15 wt % Pluronic F-127 aqueous solution was prepared, and 1 ml of the Pluronic F-127 aqueous solution was mixed with the lecithin/drug mixed solution and then lyophilized, thereby preparing drug-loaded nucleus/shell-type nanoparticles.

Separately, a sodium hyaluronate aqueous solution was prepared by adding 50 mg of sodium hyaluronate with 10 ml of distilled water, and then 2 g of drug-loaded core/shell nanoparticles was further mixed to the aqueous solution, thereby preparing a composite aqueous solution.

If necessary, the composite aqueous solution prepared above was stored by lyophilization. For use, the lyophilized product was redispersed in an aqueous solution. As a result, a temperature-sensitive composite consisting of ionic drug (bupivacaine)-loaded Pluronic F-127 nanoparticles was prepared.

Figure 8:
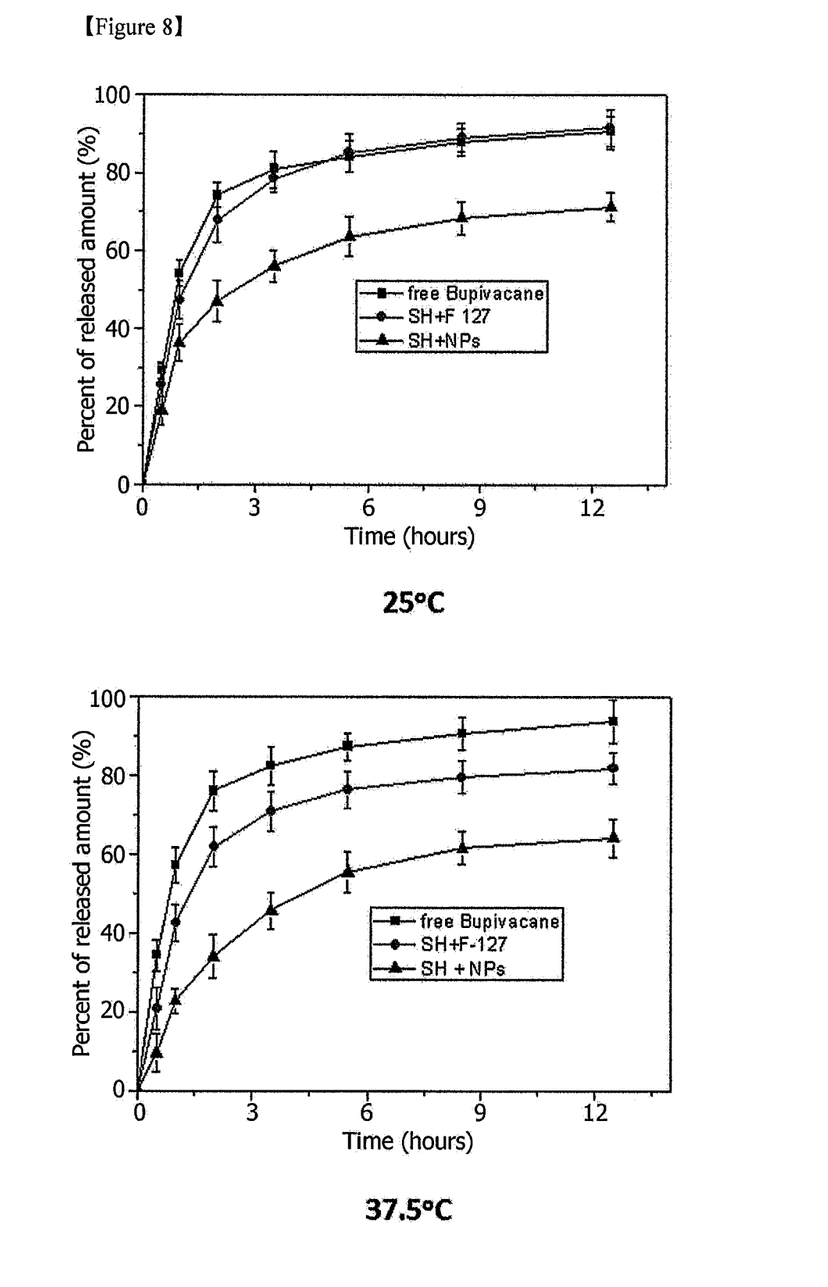
FIG. 8 is a set of graphs showing release patterns of a drug (naproxen) from composites of Example 2 and Comparative Example 2 over time at room temperature and a body temperature [SH+NPs: Example 2, SH+F-127: Comparative Example 2].

The mechanical properties of the temperature-sensitive composite were measured (FIG. 5), and a change in drug release over time was measured (FIG. 8).

Example 3: Preparation of Temperature-Sensitive Composite Which Consists of Nanoparticles Containing of Pluronic F-127 and Drug and Nanoparticles Containing of Pluronic F-68 and Drug Nanoparticles containing Pluronic F-127 and a drug were prepared using a temperature-induced phase transition method described in Korean Unexamined Patent Application Publication No. 2013-0084916.

A uniform composite was prepared by mixing 75 mg of docetaxel and 0.1 g of Solutol for 12 hours. 0.4 g of poloxamer (polyoxyethylene-polyoxypropylene-polyoxyethylene triblock copolymer, Pluronic F-127) was added to the mixture, and the subsequent mixture was heated at 70° C. for 10 minutes and stirred for 5 minutes. Then when the mixture was completely melted and had become a liquid viscous material, stirring was stopped, and the mixture was cooled at room temperature to obtain nanoparticles containing Pluronic F-127 and docetaxel.

Nanoparticles containing Pluronic F-68 and a drug were prepared using a microencapsulation method described in Korean Unexamined Patent Application Publication No. 2007-0099767 (preparation of diluent).

Using ultrasonication, a 20 wt % lecithin aqueous solution was prepared. At this time, lecithin nanoparticles having a diameter of approximately 65 nm were formed. 50 mg of doxorubicin was added to and mixed with the 1 ml of the lecithin nanoparticle aqueous solution. A 15 wt % Pluronic F-68 aqueous solution was prepared, and 1 ml of the Pluronic F-68 aqueous solution was mixed with the lecithin/drug mixed solution and then lyophilized, thereby preparing drug-loaded nucleus/shell-type nanoparticles containing Pluronic F-68 and doxorubicin.

A 25 wt % aqueous solution was prepared by adding a mixture of the nanoparticles (diluent) containing Pluronic F-68 and doxorubicin and the nanoparticles containing Pluronic F-127 and docetaxel in a weight ratio of 2:8 to an aqueous solution.

If necessary, the composite aqueous solution prepared above was stored by lyophilization. For use, the lyophilized product was redispersed in an aqueous solution. As a result, a temperature-sensitive composite consisting of nanoparticles containing Pluronic F-127 and a drug and nanoparticles containing Pluronic F-68 and a drug was prepared.

Figure 9:
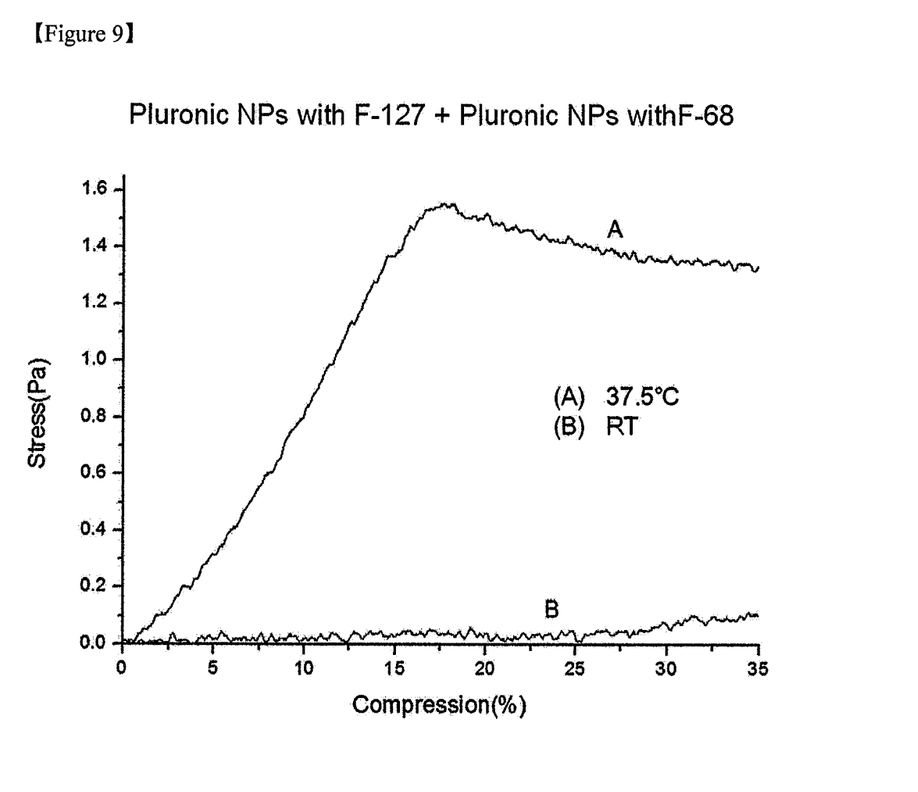
FIG. 9 is a graph showing a change in mechanical strength of a composite consisting of nanoparticles consisting of Pluronic F-127 and a drug and nanoparticles consisting of Pluronic F-68 and a drug according to Example 3 in response to temperature change from room temperature (25° C.) to a body temperature (37.5° C.).
Figure 11:
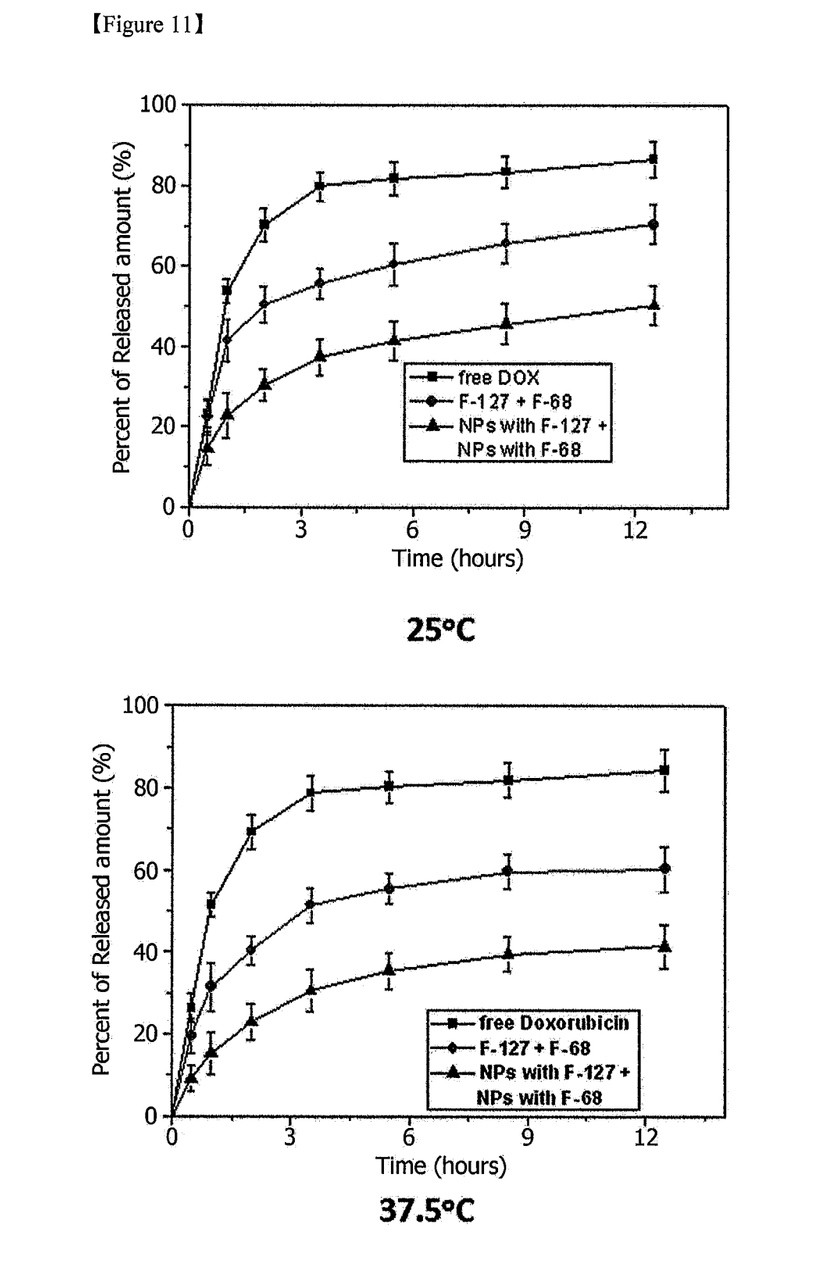
FIG. 11 is a set of graphs showing release patterns of a drug (doxorubicin) from composites of Example 3 and Comparative Example 3 over time at room temperature and a body temperature [NPs with F-127+NPs with F-68: Example 3, F-127+F-68: Comparative Example 3].
Figure 12:
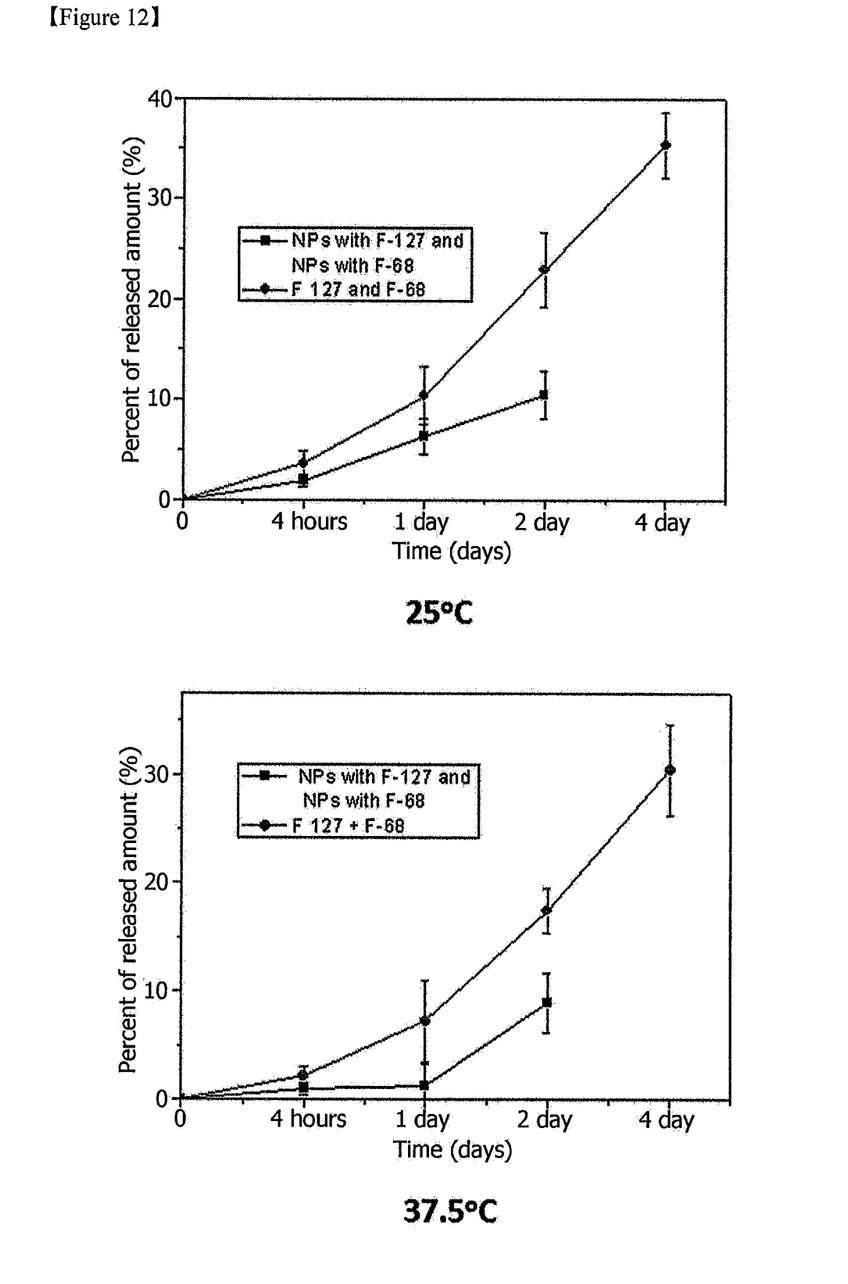
FIG. 12 is a set of graphs showing release patterns of a drug (docetaxel) from composites of Example 3 and Comparative Example 3 over time at room temperature and a body temperature [NPs with F-127+NPs with F-68: Example 3, F-127+F-68: Comparative Example 3].

The mechanical properties of the temperature-sensitive composite were measured (FIG. 9), and a change in drug release over time was measured (FIGS. 11 and 12).

Comparative Example 1: Preparation of Temperature-Sensitive Polymer Composite Consisting of Sodium Hyaluronate (SH), Pluronic F-127 and Drug (the Drug was not Loaded in Pluronic F-127)

An aqueous solution was prepared by mixing 2 g of Pluronic F-127, 0.1 g of naproxen and 50 mg of sodium hyaluronate with 10 ml of distilled water, thereby preparing a polymer composite aqueous solution in which naproxen was dispersed.

Figure 6:
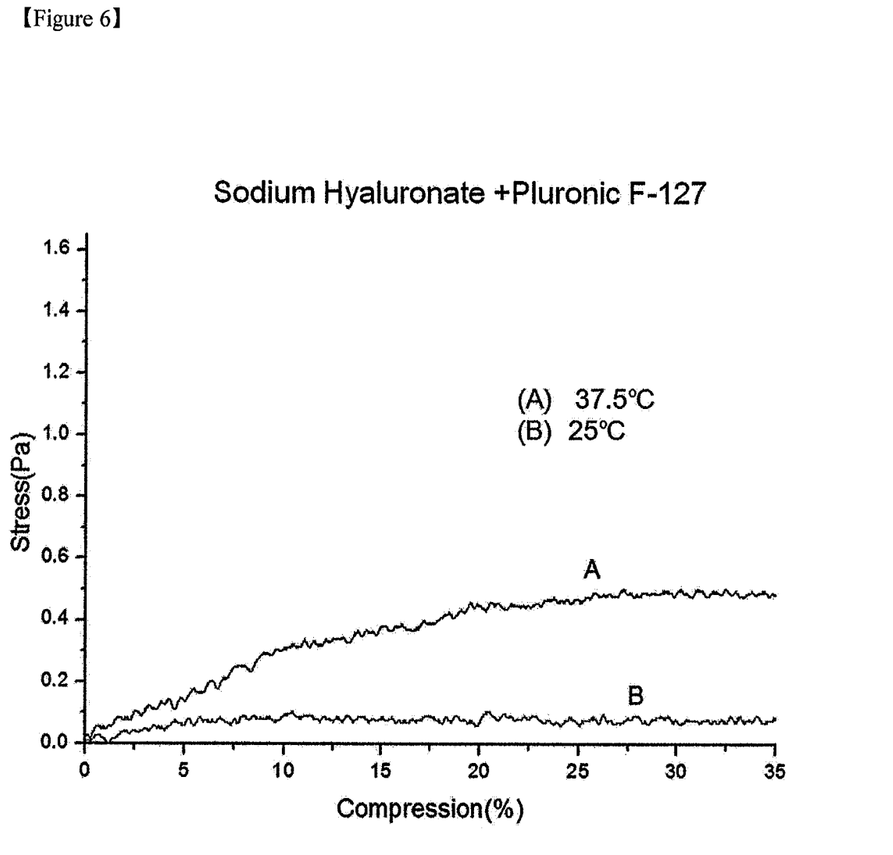
FIG. 6 is a graph showing a change in mechanical strength of a composite consisting of sodium hyaluronate, Pluronic F-127 and a drug in response to temperature change room temperature (25° C.) to a body temperature (37.5° C.) (Comparative Examples 1 and 2).

The mechanical properties of the temperature-sensitive polymer composite were measured (the result is the same as shown in FIG. 6 within an error range), and a change in drug release over time was measured (FIG. 7).

It was confirmed that, due to low solubility of naproxen, precipitation occurred in the polymer composite.

Comparative Example 2: Preparation of Temperature-Sensitive Polymer Composite Consisting of Sodium Hyaluronate (SH), Pluronic F-127 and Drug (the Drug was not Loaded in Pluronic F-127)

An aqueous solution was prepared by mixing 2 g of Pluronic F-127, 0.1 g of bupivacaine and 50 mg of sodium hyaluronate with 10 ml of distilled water, thereby preparing a polymer composite aqueous solution in which bupivacaine was dispersed.

The mechanical properties of the temperature-sensitive composite were measured (FIG. 6), and a change in drug release over time was measured (FIG. 8).

Comparative Example 3: Preparation of Temperature-Sensitive Polymer Composite Consisting of Pluronic F-68, Pluronic F-127, Doxorubicin and Docetaxel (drug was not loaded in Pluronic F-127)

An aqueous solution was prepared by mixing 1.6 g of Pluronic F-127, 0.4 g of Pluronic F-68, 50 mg of doxorubicin and 75 mg of docetaxel with 10 ml of distilled water, thereby preparing a polymer composite aqueous solution in which doxorubicin and docetaxel were dispersed.

Figure 10:
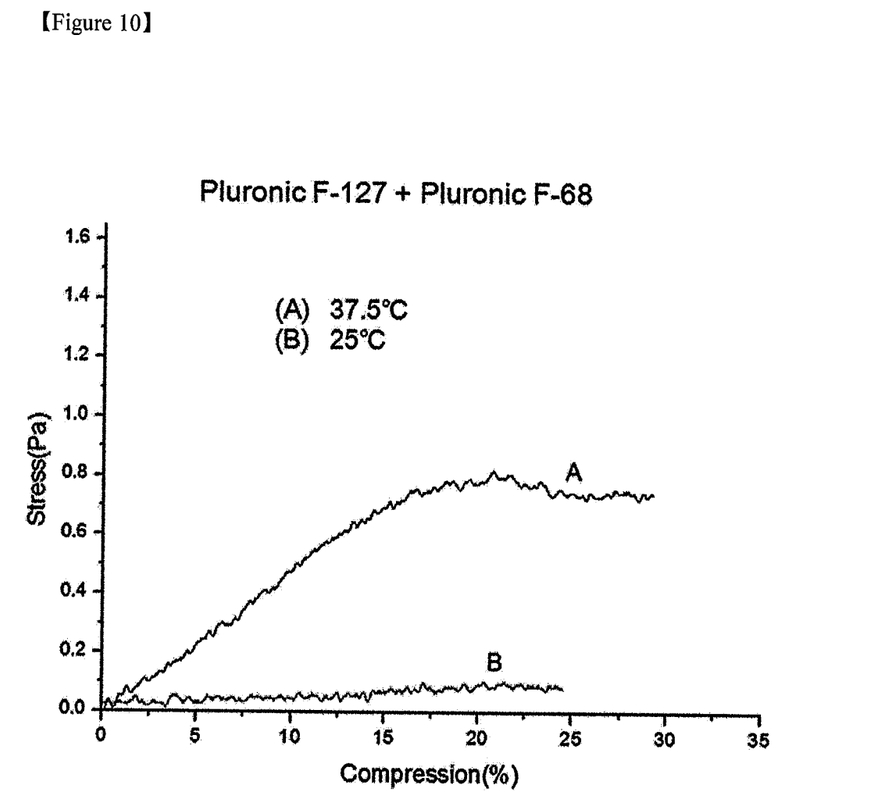
FIG. 10 is a graph showing a change in mechanical strength of a polymer composite consisting of Pluronic F-127 and Pluronic F-68 according to Comparative Example 3 in response to temperature change from room temperature (25° C.) to a body temperature (37.5° C.).

The mechanical properties of the temperature-sensitive composite were measured (FIG. 10), and a change in drug release over time was measured (FIGS. 11 and 12).

It was confirmed that, due to low solubility of docetaxel, precipitation occurred in the polymer composite.

Experimental Example 1: Change in Mechanical Properties of Temperature-Sensitive Composite Over Time A 20 wt % composite aqueous solution was prepared using each of the temperature-sensitive composites of Examples 1 and 2, the temperature-sensitive nanoparticle composite of Example 3, and the composites prepared in Comparative Examples 1, 2 and 3, and mechanical properties thereof were measured while the temperature was maintained at 25° C. and 37.5° C.

Mechanical properties of the composite were measured using an Instron 500N load cell (AG-X, Shimadzu, Japan). After the composite with a diameter of 5 mm was maintained, a pressure was vertically applied thereto from above. Here, a crosshead speed was 1 mm/minute, and a stress-strain curve was plotted (FIGS. 5, 6, 9 and 10). A higher slope obtained in the graph indicates better mechanical properties. While the temperature was maintained at a body temperature based on this, the temperature-sensitive composites of Examples 1 to 3 exhibited much higher mechanical strength than the temperature-sensitive polymer composites of Comparative Examples 1 to 3. Based on these results, the maintenance of excellent stability may be expected when the composite in the present invention is delivered into the body.

Experimental Example 2: Release Pattern of Drug Encapsulated in Temperature-Sensitive Composite To confirm the release pattern of a drug from the temperature-sensitive composite in the present invention, an experiment was carried out as follows.

20 mg of each of the temperature-sensitive composites from Examples 1, 2 and 3, and the temperature-sensitive polymer composites from Comparative Examples 1, 2 and 3 was put into a dialysis bag (filtration molecular weight cut-off—100,000), and then immersed in 20 ml of a phosphate buffer solution (PBS, pH 7.4). The temperature was maintained at 25° C. and 37.5° C. with stirring at 600 rpm. At predetermined time, 5 ml of the phosphate buffer solution was withdrawn to measure an amount of the released drug through HPLC. After sampling, the remaining phosphate buffer solution was completely removed, and a fresh phosphate buffer solution was added.

Referring to the experimental results (FIGS. 7, 8, 11 and 12), the release of the water-soluble drugs, bupivacaine (FIG. 8) and doxorubicin (FIG. 11), was decreased due to the formation of a gel at a body temperature (37° C.), and started to show a sustained release pattern. In addition, the temperature-sensitive composites of Examples 1 to 3 exhibited higher sustainability than the temperature-sensitive polymer composites of Comparative Examples 1 to 3.

In addition, the hydrophobic drugs (naproxen and docetaxel) were precipitated in the temperature-sensitive polymer composites from Comparative Examples 1 to 3 because of the low solubility in the aqueous media, and therefore the experiment could not be continued (see FIGS. 7 and 12). Therefore, in the case of the temperature-sensitive composite from Example 1, the stability and solubility in the aqueous solution were maintained by loading the hydrophobic drugs in the nanoparticles, and thus higher functionality was exhibited compared with the conventional temperature-sensitive polymer composite.

The invention claimed is:

1. A temperature-sensitive composite comprising:
   1) nanoparticles including a poorly-soluble drug-loaded with a PEO-PPO-PEO copolymer, the PEO-PPO-PEO copolymer exhibits a temperature-induced phase transition and is selected from the group consisting of Pluronic F-127, Pluronic F-188, Pluronic F-237, Pluronic F-338, Pluronic F-407, and combinations thereof; and
   2) a diluent capable of controlling viscosity; the diluent is nanoparticles including a water-soluble drug-loaded with a biocompatible and water-soluble polymer, the biocompatible and water-soluble polymer is selected from the group consisting of Pluronic F-68, and polyvinyl acetate,
   wherein the temperature-sensitive composite is maintained in a sol state at room temperature, is gelated at the time of delivery in the body, and sustains drug release;
   wherein the poorly-soluble drug is selected from the group consisting of docetaxel and naproxen;
   wherein the water-soluble drug is doxorubicin.

2. A method for preparing a temperature-sensitive composite comprising:
   preparing nanoparticles including a poorly-soluble drug-loaded with a PEO-PPO-PEO copolymer, the PEO-PPO-PEO copolymer exhibits a temperature-induced phase transition and is selected from the group consisting of Pluronic F-127, Pluronic F-188, Pluronic F-237, Pluronic F-338, Pluronic F-407, and combinations thereof; and
   mixing the nanoparticles with a diluents capable of controlling viscosity, the diluent is nanoparticles including a water-soluble drug-loaded with a biocompatible and water-soluble polymer, the biocompatible and water-soluble polymer is selected from the group consisting of Pluronic F-68, and polyvinyl acetate;
   wherein the temperature-sensitive composite is maintained in a sol state at room temperature, is gelated at the time of delivery in the body and sustains drug release;
   wherein the poorly-soluble drug is selected from the group consisting of docetaxel and naproxen;
   wherein the water-soluble drug is doxorubicin.

* * * * *